United States Patent [19]

Whitten et al.

[11] Patent Number: 4,939,258

[45] Date of Patent: Jul. 3, 1990

[54] CYCLOALKANOL ESTERS OF DIHYDROLYSERGIC ACID

[75] Inventors: Kathleen R. Whitten, Zionsville; William L. Garbrecht, Indianapolis; Gifford P. Marzoni, Indianapolis; C. John Parli, Indianapolis, all of Ind.

[73] Assignee: Eli Lilly and Company, Indianapolis, Ind.

[21] Appl. No.: 463,171

[22] Filed: Jan. 10, 1990

Related U.S. Application Data

[62] Division of Ser. No. 336,280, Apr. 11, 1989, Pat. No. 4,906,639, Division of Ser. No. 43,780, Apr. 29, 1987, Pat. No. 4,845,224, which is a division of Ser. No. 782,337, Oct. 1, 1985, Pat. No. 4,683,236.

[51] Int. Cl.$^5$ .................... C07D 457/04; A61K 31/48
[52] U.S. Cl. ........................................ 546/69; 546/67; 546/68
[58] Field of Search ............................ 546/69, 67, 68

[56] References Cited

U.S. PATENT DOCUMENTS

| 3,113,133 | 12/1963 | Hofmann et al. | 546/69 |
| 3,183,234 | 5/1965 | Garbrecht et al. | 546/69 |
| 3,228,941 | 1/1966 | Bernardi et al. | 546/69 |
| 3,228,945 | 1/1966 | Camerino et al. | 546/69 |
| 3,249,617 | 5/1966 | Hofmann et al. | 546/69 |
| 3,278,940 | 1/1966 | Bosisio et al. | 546/69 |
| 3,580,916 | 5/1971 | Garbrecht | 546/69 |
| 4,230,859 | 10/1980 | Rucman | 546/69 |

FOREIGN PATENT DOCUMENTS 122044 10/1984 European Pat. Off. .

OTHER PUBLICATIONS

Misner, Chem. Abst. 107-78140t (1987).
Garbrecht et al, Chem. Abst. 108-22133w (1988).
Garbrecht et al, Chem. Abst. 108-112812w (1988).
Cohen et al., J.P.E.T., 227, 327 (1983) (Cohen I).
Cohen et al., ibid, 232, 770 (1984) (Cohen II).
Lemberger et al., *Life Sci.*, 35, 71 (1984).
Cohen et al., *Drug Dev. Res.*, 5, 313 (1985) (Cohen IV).
Hingten et al., Abstract 37.4, *Soc. for Neurosci.* (13th Annual Meeting, Nov. 1983).

*Primary Examiner*—Cecilia Shen
*Attorney, Agent, or Firm*—William C. Martens; Leroy Whitaker

[57] ABSTRACT

Cycloalkyl or ketocycloalkyl esters of 1-substituted-6-$C_{1-4}$ straight chain alkyl (or allyl)-ergoline-8β-carboxylic acids, useful as 5HT receptor antagonists.

1 Claim, No Drawings

CYCLOALKANOL ESTERS OF DIHYDROLYSERGIC ACID

This application is a division of application Ser. No. 336,280 filed 4-11-89 now U.S. Ser. No. 4,906,639 which is a division of application Ser. No. 07/043,780, filed 4-29-87 now U.S. Pat. No. 4,845,224; which is a division of application Ser. No. 06/782,337 filed 10-11-85 now U.S. Pat. No. 4,683,236.

BACKGROUND OF THE INVENTION

Garbrecht, U.S. Pat. No. 3,580,916, discloses a group of lysergic (I) and 9,10-dihydrolysergic acid (II) esters formed with various open chain and cyclic diols. The following structures summarize the disclosure in Garbrecht.

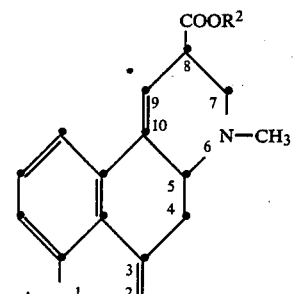

I and

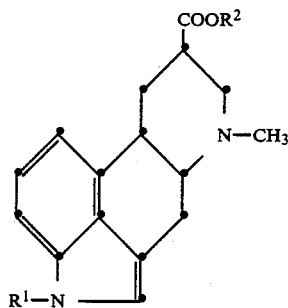

II wherein $R^1$ is H, $C_{1-3}$ alkyl, allyl or benzyl and $R^2$ is $C_2$–$C_8$ monohydroxyalkyl, $C_{2-8}$ dihydroxyalkyl or $C_{5-11}$ monohydroxycycloalkyl having from 5–8 ring carbons. The compounds are useful as serotonin antagonists, the patent stating that "In animals, the compounds act as neurosedatives . . . and are therefore useful in calming . . . animals". The use of compounds according to II wherein $R^2$ is mono or dihydroxyalkyl in migraine and other disease states characterized by an excess of peripheral 5HT is disclosed in EPO 122,044 published 10-17-84.

The $R^2$ group of Garbrecht in I or II when it is hydroxycycloalkyl is formed by the reaction of a cycloalkyldiols with an "activated" form of lysergic or dihydrolysergic acid. The following list of illustrative cycloalkyldiols is from Garbrecht.
cyclopentane-1,3-diol,
cyclohexane-1,4-diol,
5,5-dimethylcyclohexane-1,3-diol,
2-ethylcyclopentane-1,3-diol,
cycloheptane-1,2-diol,
4-methylcycloheptane-1,2-diol,
cyclooctane-1,5-diol,
3-ethylcyclooctane-1,3-diol,
4-isopropylcycloheptane-1,2-diol,
3-propylcyclooctane-1,5-diol,
3-isopropylcyclooctane-1,5-diol Recently, interest in the Garbrecht compounds has been intensified by the finding that they had excellent peripheral serotonin antagonist activity against $5HT_2$ receptors and did not interact, either as agonists or antagonists, with other receptors, particularly $alpha_2$ receptors.

The most active peripheral serotonin antagonist from Garbrecht was 1-isopropyl-6-methyl-8β-(1-methyl-2-hydroxy)propoxycarbonyl-5R-ergoline (II in which $R^1$ is isopropyl and $R^2$ is 1-methyl-2-hydroxypropyl). In the above name, 5R refers to the beta orientation of the C-5 hydrogen. The C-10 hydrogen is alpha—10R, and the beta orientation at C-8 is the same as in either lysergic or 9,10-dihydrolysergic acid, both of which acids have a 6-methyl group. An alternate name for the above compound is 1-isopropyl-9,10-dihydrolysergic acid 1-methyl-2-hydroxypropyl ester. Cohen et al. *J.P.E.T.*, 227, 327 (1983) (Cohen I) reported that the above compound, given the code number LY53857, was a potent antagonist of vascular contraction to serotonin, which effect is mediated by $5HT_2$ receptors. The compound had minimal affinity for vascular alpha adrenergic, dopaminergic and histaminergic receptors ($K_{dissoc.} \approx 10^{-10}$ vs $\approx 10^{-5}$). Other papers on the pharmacologic properties of LY53857 include Cohen et al, *J.P.E.T.*, 232, 770 (1985) (Cohen III), Harriet Lemberger et al., *Life Sciences*, 35, 71 (1984), and Cohen, *Drug Development Res.*, 5, 313 (1985), (Cohen IV). Cohen and Fuller, EPO 122,044, published 10-17-84, covers the use of hydroxyalkyl esters of 1-alkyl dihydrolysergic acid as peripheral $5HT_2$ receptor antagonists.

Four additional examples of ergolines with a substituent on the indole nitrogen are: U.S. Pat. No. 3,113,133, Hofmann et al., which discloses and claims esters and amides carrying an indole N substituent such as a lower alkyl or alkenyl group or an aralkyl group. The compounds are said to be useful as serotonin antagonists, in treating inflammatory, arthritic and allergic diseases and in treating carcinoid syndrome.

U.S. Pat. No. 3,249,617, Hofmann et al., which covers (indole) N-alkyl or allyl lysergic acids, useful as intermediates.

U.S. Pat. No. 3,228,941, Bernardi et al., which discloses and claims a group of (indole) N-methylergolines —amides, hydroxamides and amidines. The compounds are alleged to have oxytoxic, adrenolytic, hypotensive, sedative and antienteraminic action.

U.S. Pat. No. 4,230,859 to Rucman which discloses dihydrolysergic acid carrying a $C_{1-5}$ alkyl group on the indole nitrogen, useful as intermediates.

Finally, ergolines actually used in the treatment of migraine include the amides: ergotamine, methysergide and ergonovine.

None of the above references indicate that a cycloalkanol ester of an N-alkylated dihydrolysergic acid would have peripheral serotonin antagonist properties.

SUMMARY OF THE INVENTION

This invention provides ergolines of the formula:

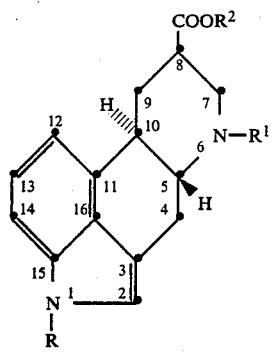

wherein R is primary or secondary $C_{1-8}$ alkyl, $CH_2-C_{2-4}$ alkenyl, $C_{3-8}$ cycloalkyl or $C_{3-6}$ cycloalkyl-substituted $C_{1-5}$ primary or secondary alkyl, the total number of carbon atoms in R not to exceed 8; $R^1$ is allyl, H or $C_{1-4}$ straight-chain alkyl; i.e., methyl, ethyl, n-propyl or n-butyl, and $R^2$ is $C_{5-7}$ cycloalkyl, or keto-substituted $C_{5-7}$ cycloalkyl; and pharmaceutically acceptable acid addition salts thereof. Compounds according to III, wherein $R^1$ is other than H, are central or peripheral serotonin $5HT_2$ receptor antagonists lacking interaction, at $5HT_2$ blocking doses, with other receptors. Compounds wherein $R^1$ is H are primarily intermediates.

Groups which R represents include methyl, ethyl, allyl, n-propyl, isopropyl, crotyl, methallyl, n-hexyl, sec-amyl, sec-octyl, n-heptyl, 2,4-dimethylpentyl, 2-ethylpentyl, cyclopropyl, cyclopropylmethyl, cyclopentyl methyl, 2-cyclobutyl ethyl, cyclohexyl, isobutyl, sec.-butyl, 3-methyl-2-butyl, isoamyl, 2-methylhexyl, 3-methylhexyl, 4-methylhexyl(isohexyl), 2-hexyl, 3-hexyl, n-heptyl, 2-heptyl, 3-heptyl, 4-heptyl, n-octyl, 2-octyl, 3-octyl, 4-octyl, isooctyl, 2-methylheptyl, 3-methyl-2-heptyl, and the like. Illustrative of the groups which $R^2$ represents include cyclohexyl, 3-ketocyclohexyl, cyclopentyl, 3-ketocycloheptyl, cycloheptyl, 3-ketocyclopentyl, 4-ketocyclohexyl, 2-ketocycloheptyl and the like.

Compounds according to the above formula are named as ergoline derivatives in which the trans(−) or 5R,10R configuration of the bridgehead hydrogens is specified (The same configuration as in the naturally-occurring 9,10-dihydro ergot alkaloids). In U.S. Pat. No. 3,580,916, a different naming system is used; the basic ring system is named as a 6aR,10aR-4,6,6a,7,8,9,10,10a-octahydroindolo[4,3-f,g]quinoline. Illustratively, by the alternate naming system, 9,10-dihydrolysergic acid becomes 6aR,10aR-7-methyl-4,6,6a,7,8,9,10,10a-octahydroindolo[4,3-f,g]quinoline-9β-carboxylic acid. Another equally valid name for dihydrolysergic acid is 6-methyl-8β-carboxyergoline since the name "ergoline" specifies the orientation of the bridgehead hydrogens.

When $R^1$ is other than methyl, we prefer to use the trivial name "ergoline" with the numbering system specified in III above, but when $R^1$ is methyl, we will use the 9,10-dihydrolysergic acid nomenclature.

Pharmaceutically-acceptable acid addition salts of the compounds of formula III include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Illustrative compounds of this invention include:

1,6-diethyl-8β-cyclohexyloxycarbonylergoline succinate 1-methyl-6-ethyl-8β-cyclopentyloxycarbonylergoline hydrochloride 1-n-propyl-6-allyl-8β-cycloheptyloxycarbonylergoline sulfate 1-isopropyl-6-n-propyl-8β-(2-oxo)cyclohexyloxycarbonylergoline hydrobromide 1-allyl-6-ethyl-8β-(4-oxo)cycloheptyloxyergoline tartrate and the like.

The preparation of compounds represented by formula III when $R^2$ is methyl (esters of 9,10-dihydrolysergic acid) above is the general method of U.S. Pat. No. 3,580,916. According to this procedure, 9,10-dihydrolysergic acid is first alkylated on the indole nitrogen using standard procedures—base plus an aliphatic halide. Liquid ammonia is a convenient solvent with sodamide as the base and an alkyl or cycloalkyl or cycloalkylalkyl iodide or $C_{2-4}$ alkenyl-$CH_2$ chloride or bromide as the alkylating or alkenylating agent. (See also U.S. Pat. No. 3,183,234-Garbrecht and Lin which contains general directions and a specific example of the above alkylation procedure).

Alternatively, the procedure of Marzoni, Ser. No. 782,339 filed this even date may be employed. According to this procedure, an aryl sulfonate of the structure R-O-$SO_2$-phenyl-Y wherein R has its previous meaning and Y is H, $CH_3$, Br or $NO_2$, is reacted with 9,10-dihydrolysergic acid in the presence of an alkali metal hydroxide, suitably KOH, in an aprotic solvent, conveniently DMSO.

With the indole nitrogen substituent in place, the next step in the synthetic procedure is esterification. This procedure requires relatively mild reaction conditions according to U.S. Pat. No. 3,580,916. The reaction is, however, an otherwise standard acid-catalyzed esterification. The free acid and cycloalkanol or ketocycloalkanol are the reactants and a convenient work-up of the esterification mixture involves partitioning between water and a water-immiscible solvent; $(CH_2Cl)_2$ for example. It should be noted that the cycloalkanol or ketocycloalkanol should be a secondary alcohol, and not a tertiary alcohol.

If the final product is not a 9,10-dihydrolysergic acid ester, but is a 6-ethyl, 6-n-propyl, 6-n-butyl or allyl derivative, the replacement of the 6-methyl group of 9,10-dihydrolysergic acid must take place prior to esterification with the cycloalkanol or ketocycloalkanol; ie., on an 1-R-9,10-dihydrolysergic acid lower alkyl ester. Replacement of the 6-methyl with ethyl, n-propyl, allyl, n-butyl or the like, can be carried out by the procedure of Kornfeld and Bach, U.S. Pat. No. 4,166,182, whereby the N-methyl group is reacted with cyanogen bromide to form an N-cyano derivative. The cyano group can then be removed by hydrogenation with zinc dust in hydrochloric acid. However, we prefer to use an hydrolysis procedure using base in ethyleneglycol or other suitable high boiling solvent. The procedure also hydrolyses the 8β-ester group to the free acid. The free acid is then, esterified with a cycloalkanol or ketocycloalkanol ($R^2OH$). The resulting ester containing a secondary amine group can then be alkylated or allylated in DMF solution in the presence of a base such as sodium carbonate, giving a final product according to formula III wherein $R^1$ is other than methyl.

This procedure is graphically illustrated in Reaction Scheme 1 below,

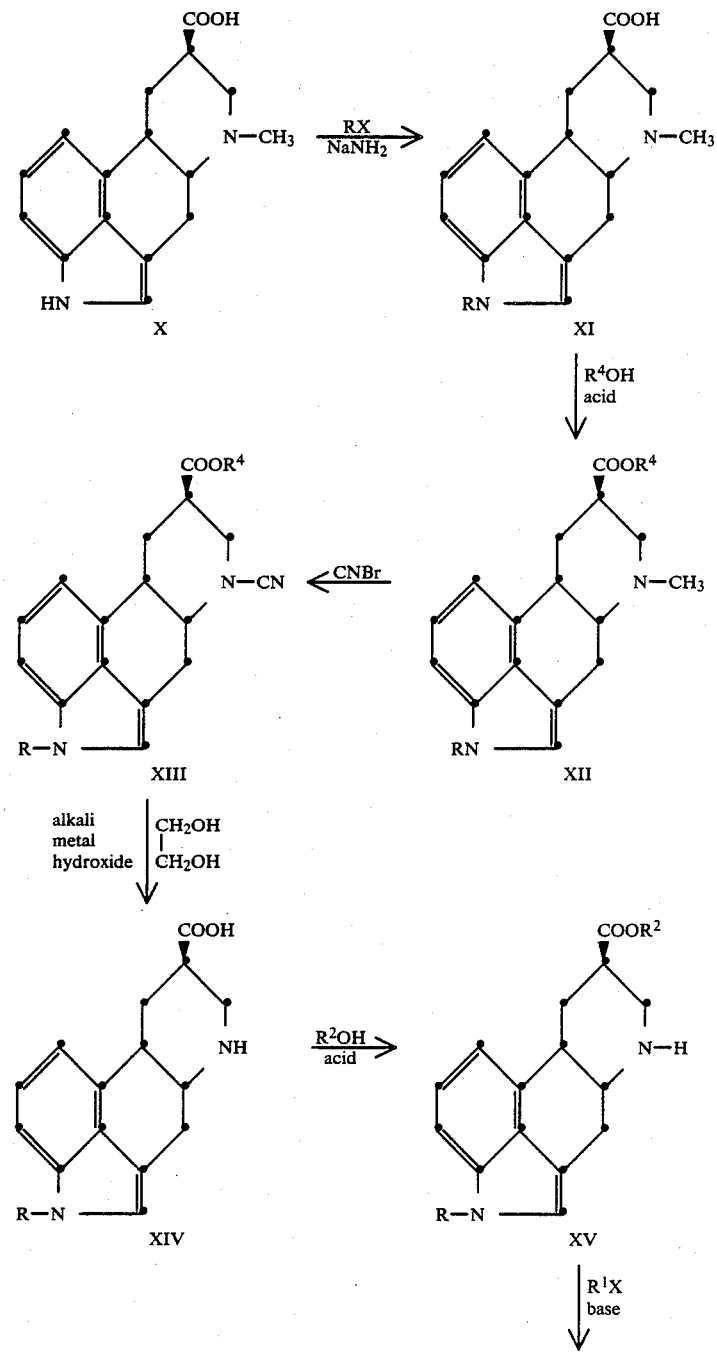

Reaction Scheme 1

-continued

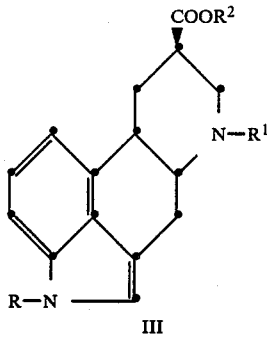

In the above Reaction Scheme, 9,10-dihydrolysergic acid (X) is alkylated on the indole nitrogen with a primary or secondary $C_{1-8}$ alkyl, a $CH_2$–$C_{2-4}$ alkenyl, a $C_{3-8}$ cycloalkyl or a $C_{3-6}$ substituted $C_{1-5}$ primary or secondary alkyl halide using sodamide to create the reactive anion. The N-substituted product (XI) is then esterified with a lower alkanol $R^4OH$ (a $C_{1-2}$ alkanol preferably) to yield the N-substituted ester (XII). This ester is then reacted with CNBr by standard procedures to replace the methyl group and form an N-cyano derivative (XIII). Removal of the cyano group under the preferred basic conditions yields a 1-R-9,10-dihydro-6-desmethyllysergic acid (XIV), since the basic conditions also saponifies the C-8 ester group. Next, the N-R-6-desmethyldihydrolysergic acid is re-esterified with a desired $C_{5-7}$ cycloalkanol or 4-oxo $C_{5-7}$ cycloalkanol to yield the $N^6$-desmethyl ester (XV). The piperidine ring nitrogen ($N^6$) is then realkylated with a $C_{1-4}$ alkyl or allyl halide and base under standard conditions to yield the compounds of this invention (III).

It might seem redundant to realkylate at $N^6$ with a methyl group since that group is present in the 9,10-dihydrolysergic acid starting material. However, the process would enable one to insert a "tagged" ($C^{14}$ or $H^3$) methyl group for metabolic studies.

Although the above reaction sequence has been illustrated with reference to preparing cycloalkyl or ketocycloalkyl esters, it is apparent that the procedure is readily adaptable to the provision of 1-substituted-6-alkylergoline-8β-carboxylic acid esters formed with open chain diols, or alkoxyalkanols, dialkoxyalkanols or ketoalkanols of the formula $R^6$—$CHR^5OH$ wherein $R^5$ is H, $CH_2$—O —$C_{1-3}$ alkyl or $CH_3$ and $R^6$ is hydroxy-$C_{1-3}$ alkyl, alkoxy-$C_{1-3}$ alkyl, di($C_{1-3}$ alkyloxy $C_{1-3}$ alkyl or keto $C_{1-3}$ alkyl.

Alternatively, ergoline-8β-carboxylic acid (6-desmethyl-9,10-dihydrolysergic acid) can be substituted at N-1, esterified with $R^2OH$ and then alkylated or allylated at N-6.

The following examples illustrate the preparation of compounds according to III above.

EXAMPLE 1

Preparation of Cyclohexyl 1-Isopropyl-9,10-dihydrolysergate (1-Isopropyl-6-methyl-8β-cyclohexyloxycarbonylergoline)

A reaction mixture, prepared from 12.5 g of 1-isopropyl-9,10-dihydrolysergic acid (from Garbrecht, and Lin, U.S. Pat. No. 3,183,234), 50 ml of cyclohexanol, and 7.6 g of p-toluenesulfonic acid, was heated at about 90° C. for 24 hours. The reaction mixture was cooled and the cooled mixture partitioned between $(CH_2Cl)_2$ and dilute aqueous ammonium hydroxide (pH=10). The organic layer was separated and the separated layer washed with water and then dried. Evaporation of the solvent in vacuo yielded a residue comprising cyclohexyl 1-isopropyl-9,10-dihydrolysergate formed in the above reaction. The free base was dissolved in methanol and an equivalent of maleic acid added. Ether was added and a crystalline maleate salt was obtained, which salt was separated by filtration. Two recrystallizations from a methanol/ether solvent mixture gave cyclohexyl 1-isopropyl-9,10-dihydrolysergate maleate melting at 203°–5° C.; $[\alpha]_D^{25} = -51.7°$ (1% methanol); yield=7.1 g (2 crops); Mass spectrum; m/e at 394 (free base).

Analysis: Calc.: C, 68.21; H, 7.50; N, 5.49; Found: C, 67.96; H, 7.71; N, 5.29.

EXAMPLE 2

Preparation of 1-Isopropyl-6-ethyl-8β-cyclohexyloxycarbonylergoline

Following the procedure of Example 1, 1.5 g of 1-isopropylergoline-8β-carboxylic acid were esterified with 15 g of cyclohexanol in the presence of 1.5 g of p-toluenesulfonic acid to yield 1-isopropyl-8β-(cyclohexyloxycarbonyl)ergoline. The product, 1.91 g of an oil, was converted to the maleate salt in a 6:1 ether/ethyl acetate solvent mixture. The salt was isolated by evaporation and then recrystallized from ether/methanol; yield=0.93 g of cyclohexyl 1-isopropyl-8β-(cyclohexyloxycarbonyl)ergoline maleate (96.77% pure by HPLC); molecular ion at 380; $[\alpha]_{25}^D = -40.64°$.

Analysis: Calc.: C, 67.72; H, 7.31; N, 5.64; Found: C, 67.95; H, 7.54; N, 5.36.

Two grams of 1-isopropyl-8β-cyclohexyloxycarbonylergoline maleate were converted to the free base by partitioning between 100 ml of $(CH_2Cl)_2$ and 100 ml. of saturated aqueous sodium bicarbonate. The free base passed into the organic layer. The organic layer was separated and the solvent evaporated therefrom. The resulting residue was dissolved in 15 ml of DMF, and 0.67 g of potassium carbonate and 0.75 g of ethyl iodide added to the solution. This reaction mixture was stirred at ambient temperature for about 3 days at which time HPLC indicated that starting material was no longer present. The reaction mixture was partitioned between 50 ml ethyl acetate and 50 ml of water. The organic layer was separated and the separated layer twice extracted with 50 ml portions of water. The organic layer was dried and the solvent removed by evaporation. The resulting residue (weight=1.67 g) comprising cyclohexyl 1-isopropyl-6-ethyl-8β-cyclohexyloxycarbonylergoline formed in the above reaction, was converted to the corresponding hydrochloride salt in ethyl acetate solution with gaseous HCl. Two crops of the crystalline salt were recovered by filtration; yield=1.42 g; purity by HPLC>99.2%. The crystalline fraction was slurried in a THF/ether solvent mixture and the slurry filtered. 1-Isopropyl-6-ethyl-8β-cyclohexyloxycarbonylergoline hydrochloride thus prepared melted above 220° C.; yield=1.33 g; molecular ion at 408.

Analysis (block dried); Calc.: C, 70.17; H, 8.38; N, 6.29; Found: C, 70.02; H, 8.50; N, 6.47.

Other 6-alkyl derivatives of cyclohexyl 1-iso-propyl-8β-cyclohexyloxycarbonylergoline prepared by the above reaction sequence include 1-Isopropyl-6-n-propyl-8β-cyclohexyloxyergoline hydrochloride; yield=1.14 g (from 2.0 g starting material); mp>220° C.; purity >98.6%; molecular ion at 422;

Analysis (block dried); Calc.: C, 70.64; H, 8.56; N, 6.10; Found: C, 70.41; H, 8.51; N, 6.36.

1-Isopropyl-6-n-butyl-8β-cyclohexyloxycarbonyl ergoline hydrochloride; yield=1.45 g (purity >99.1%); mp >220° C.; molecular ion at 436;

Analysis (block dried); Calc.: C, 71.09; H, 8.74; N, 5.92; Found: C, 70.85; H, 8.62; N, 5.66.

EXAMPLE 3

Preparation of 4-Oxocyclohexyl 1-isopropyl-9,10-dihydrolysergate

Following the procedure of Example 1, 3.12 g of 1-isopropyl-9,10-dihydrolysergic acid were esterified with 1.2 g of 4-oxocyclohexanol in the presence of 4 ml of triethylamine and 3.83 g of methyl 2-chloropyridinium chloride in 10 ml of $CH_2Cl_2$. The reaction mixture was refluxed for 3 hours and stirred overnight at room temperature. Water and $(CH_2Cl)_2$ were added. The organic layer was separated and the solvent evaporated therefrom to leave a brown oil comprising 4-oxocyclohexyl 1-isopropyl-9,10-dihydrolysergate free base formed in the above reaction. The free base was converted to the maleate salt as in Example 2. Recrystallization of the salt from acetone/ether and then methanol/ether gave 0.05 g of crystalline material salt; 0.03 g of free base of 95.5% purity were also recovered; molecular ion at 408.

Useful starting material for the above reactions are prepared as follows.

Preparation 1

Preparation of 4-Hydroxycyclohexanone.

Four grams of 4-methoxycyclohex-3-en-1-ol were dissolved in 50 ml of $CHCl_3$. About 0.01 g of p-toluenesulfonic acid were added and the reaction mixture stirred at room temperature for about 1 hour. The reaction mixture was the washed with 50 ml of water. The $CHCl_3$. layer was separated and dried and the volatile constituents removed therefrom in vacuo. The product of the reaction, 4-oxocyclohexanol, was used without further purification.

Preparation 2

Preparation of 1-Isopropylergoline-8β-carboxylic acid

A reaction mixture was prepared by adding 1.6 ml of 18M sulfuric acid to a mixture of 50 g of 1-isopropyl-9,10-dihydrolysergic acid (prepared according to the procedure of column 3, U.S. Pat. No. 3,103,234) and 500 ml of methanol. The esterification mixture was stirring overnight at room temperature. TLC (18:6:1 $CHCl_3$/MeOH/acetic acid) indicated the esterification was complete. About ⅓ of the MeOH was removed by evaporation. 600 ml of saturated aqueous sodium bicarbonate were added (pH=8–9). The alkaline mixture was filtered and the fiter cake dried; yield of methyl 1-isopropyl-9,10-dihydrolysergate was 40.1 g (98% pure by LC.).

A reaction mixture was prepared from 39.9 g of methyl 1-isopropyl-9,10-dihydrolysergate, 14.8 g of CNBr and 400 ml of $CH_2Cl_2$. The reaction mixture was stirred at room temperature overnight, by which time TLC (same solvent system as above) indicated absence of starting material. Evaporation of the volatile constituents gave a solid residue (wt=46.7 g) comprising methyl 1-isopropyl-6-cyanoergoline-8β-carboxylate formed in the above reaction. The residue was dissolved in 460 ml of refluxing MeOH and the hot solution filtered. Crystals formed in the filtrate, which was then chilled overnight. The crystals were filtered and the filter cake washed with MeOH. Methyl 1-isopropyl-6-cyanoergoline thus prepared was one spot material; yield=35.3 g. NMR confirmed the structure.

A reaction mixture was prepared by combining 25 g of methyl 1-isopropyl-6-cyanoergoline-8β-carboxylate. 8.89 NaOH pellets and 250 ml of ethylene glycol. The reaction mixture was heated in the range 130°–40° C. for about 3 hours. 750 ml of water were added. The pH of the resulting solution was adjusted to about 5 with glacial acetic acid (30 mls.). Crystals began to form and the solution was chilled overnight. The crystals were separated by filtration and the filter cake washed with water; yield (after drying)=19.6 g of 1-isopropylergoline-8β-carboxylic acid, (97.3% pure by HPLC).

This invention also provides novel methods whereby 5HT receptors are blocked. Such methods are potentially useful in treating disease states in which an excess of circulating serotonin is a major contributing cause. These disease states include hypertension, anorexia nervosa, depression, mania, thrombosis, carcinoid syndrome, migraine and vasospasm. The compounds according to III above show relatively slight affinity for other receptors, $\alpha_1$, $\alpha_2$, $\beta$, histamine, carbachol etc. and thus are highly selective in their action. Formulations in which a compound of this invention is an active ingredient also form another aspect of this invention.

In order to demonstrate that compounds according to formula III have an extremely high affinity for $5HT_2$ receptors, apparent dissociation constants ($K_B$) as a measure of affinity for $5HT_2$ receptors, expressed as the negative logarithm, have been determined according to the following protocol.

Male Wistar rats (150–300 gram weight) were killed and their external jugular veins and thoracic aortas dissected free of connective tissue, cannulated in situ and placed in a modified Krebs' bicarbonate buffer in a suitable tissue bath. Two L-shaped 30-gauge stainless-steel hypodermic needles were inserted in each cannula and the dissected vessels gently pushed onto the needles. One needle was attached with thread to a stationary glass rod and the other to the transducer. [The procedure employed was that described by Hooker, Calkins and Fleisch, *Blood Vessels*, 14, 1, (1977) for use with circular smooth muscle preparations.]

The modified Krebs' bicarbonate buffer had the following makeup: (concentrations in millimoles): sodium chloride, 118.2; potassium chloride, 4.6; calcium chloride dihydrate, 1.6; potassium dihydrogenphosphate, 1.2; magnesium sulfate, 1.2; dextrose, 10.0; sodium bicarbonate, 24.8; and water q.s. to 1000 g. The tissue baths were maintained at 37° C. and were aerated with 95% oxygen-5% CO$_2$. An initial optimum resting force of 1 and 4 g was applied to the jugular vein and aorta, respectively. Isometric contractions were recorded as changes in grams of force on a Beckman Dynograph with Statham UC-3 transducers and microscale accessory attachment. Tissues were allowed to equilibrate 1 to 2 hours before exposure to drugs. Control responses to serotonin in the jugular vein and to norepinephrine in the aorta were obtained. The vessels were then incubated with appropriate concentrations of antagonist for one hour. Responses to serotonin or to norepinephrine were then repeated in the presence of the antagonist. Contraction to serotonin was evaluated in the jugular vein since this tissue produces marked responses to serotonin in the absence of alpha receptors—see Cohen and Wiley, *J. Pharm. Exp. Ther.*, 205, 400 (1978). Alpha receptor antagonist activity was evaluated in the aorta.

Apparent antagonist dissociation constants were determined for each concentration of antagonist according to the following equation:

$$K_B = \frac{[B]}{[\text{dose ratio} - 1]}$$

wherein [B] is the concentration of the antagonist and the dose ratio is the ED$_{50}$ of the agonist in the presence of the antagonist divided by the control ED$_{50}$. These results are then expressed as the negative logarithm of K$_B$. The $-\log$ K$_B$ values obtained for compounds of this invention are given below in Table 1.

TABLE 1

Apparent Dissociation Constants for 5HT$_2$ receptors determined in the rat jugular vein.

| Compound | | | 5HT$_2$ |
|---|---|---|---|
| R$^1$ | R$^2$ | salt | $-\log$ K$_b$ ± S.E. |
| CH$_3$ | cyclohexyl | maleate | 8.67 ± S.E. |
| CH$_3$ | 4-oxocyclohexyl | maleate | 10.01 ± 0.08 |
| C$_2$H$_5$ | cyclohexyl | HCl | 7.81 ± 0.17 |
| n-C$_3$H$_7$ | cyclohexyl | HCl | 7.07 ± 0.05 |
| n-C$_4$H$_9$ | cyclohexyl | HCl | 7.4 ± 0.19 |

In mammals, hypertension may be mediated through 5HT$_2$ receptors. Thus, compounds of formula III would be expected to lower blood pressure in humans as does ketanserin, another 5HT$_2$ blocker, but without the side effects attributable to alpha adreneric receptor blockade of ketanserin.

In carrying out our novel therapeutic process, a pharmaceutically-acceptable salt of a drug according to formula III above formed with a non-toxic acid is administered orally or parenterally to a mammal with an excess of circulatory serotonin in which mammal is desirable to block 5HT$_2$ in order to alleviate symptoms attributable to excessive serotonin levels such as high blood pressure and migraine. For parenteral administration, a water soluble salt of the drug is dissolved in an isotonic salt solution and administered by the i.v. route. For oral administration, a pharmaceutically-acceptable salt of the drug is mixed with standard pharmaceutical excipients such as starch and loaded into capsules or made into tablets, each containing 0.1 to 100 mg of active drug. Dosage levels of from 0.1–10 mg/kg have been found to be effective in blocking 5HT$_2$. Thus, the oral dosage would be administered 2–4 times per day, giving a daily dosage range of about 0.003 to about 10.0 mg./kg. per day.

Other oral dosage forms, suspensions, elixirs and tablets, can also be utilized and are preparable by standard procedures.

We claim:

1. A process for preparing a compound of the formula:

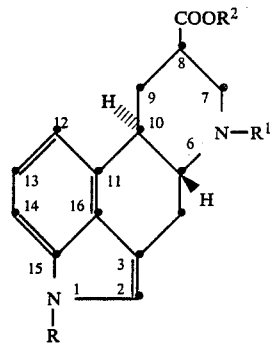

wherein R is primary or secondary C$_{1-8}$ alkyl, CH$_2$–C$_{2-4}$ alkenyl, C$_{3-8}$ cycloalkyl or C$_{3-6}$ cycloalkyl-substituted C$_{1-5}$ primary or secondary alkyl, the total number of carbon atoms in R not to exceed 8; R$^1$ is H, allyl or C$_{1-4}$ straight chain alkyl, and R$^2$ is C$_{5-7}$ cycloalkyl or keto-substituted C$_{5-7}$ cycloalkyl, which comprises (A) estesrifying a 1-R-9, 10-dihydrolysergic acid, wherein R$^2$ is hydrogen, with a lower alkanol;

(B) reacting the resulting lower alkanol ester with CNBr to form a lower alkyl 1-R-6-cyanoergoline-8$\beta$-carboxylate;

(C) treating the resulting 6-cyano compound with an inorganic base in a glycol solvent having a boiling point above about 140° C. to form a 1-R-ergoline-8$\beta$-carboxylic acid.

(D) reesterifying said 1-R-ergoline-8$\beta$-carboxylic acid with an alcohol selected from the group consisting of a C$_{5-7}$ cycloalkanols, C$_{5-7}$ cycloalkandiol, keto-substituted C$_{5-7}$ cycloalkanols, or an alkanol of the formula R$^6$-CHR$^5$OH wherein R$^5$ is H, CH$_2$-O-C$_{1-3}$ alkyl or CH$_3$ and R$^6$ is hydroxy C$_{1-3}$ alkyl, C$_{1-3}$ alkyloxy C$_{1-3}$ alkyl, di(C$_{1-3}$ alkyloxy) C$_{1-3}$ alkyl or keto C$_{1-3}$ alkyl-;

(E) and then racting the 1-R-ergoline-8$\beta$-carboxylic acid ester thus formed with a C$_{1-4}$ straight chain alkyl or allyl halide in the presence of base to form the corresponding 1-R-6-C$_{1-4}$ straight chain alkyl (or allyl)ergoline-8$\beta$-caraboxylic acid ester, wherein R has its previous meaning.

* * * * *